US012735755B2

(12) United States Patent
Dai et al.

(10) Patent No.: US 12,735,755 B2
(45) Date of Patent: Sep. 15, 2026

(54) COMPOSITION, KIT, AND METHOD FOR DETECTING AND TYPING CORONAVIRUSES

(71) Applicant: SANSURE BIOTECH INC., Changsha (CN)

(72) Inventors: Lizhong Dai, Changsha (CN); Deyong Tan, Changsha (CN); Zhongping Deng, Changsha (CN); Jia Liu, Changsha (CN); Bozhi Ji, Changsha (CN); Xing Cheng, Changsha (CN); Qingzhi Sun, Changsha (CN); Jin Yan, Changsha (CN)

(73) Assignee: SANSURE BIOTECH INC., Changsha (CN)

( * ) Notice: Subject to any disclaimer, the term of this patent is extended or adjusted under 35 U.S.C. 154(b) by 1000 days.

(21) Appl. No.: 17/891,291

(22) Filed: Aug. 19, 2022

(65) Prior Publication Data

US 2023/0193407 A1 Jun. 22, 2023

Related U.S. Application Data

(63) Continuation of application No. PCT/CN2020/090054, filed on May 13, 2020.

(30) Foreign Application Priority Data

Mar. 2, 2020 (CN) ........................ 202010136909.5

(51) Int. Cl.
*C12Q 1/70* (2006.01)

(52) U.S. Cl.
CPC .................................. *C12Q 1/701* (2013.01)

(58) Field of Classification Search
None
See application file for complete search history.

(56) References Cited

U.S. PATENT DOCUMENTS

| | | | |
|---|---|---|---|
| 2012/0238017 | A1 | 9/2012 | Lee et al. |
| 2016/0106854 | A1 | 4/2016 | Dunn et al. |

FOREIGN PATENT DOCUMENTS

| | | | |
|---|---|---|---|
| AU | 2006214059 | A1 | 8/2006 |
| CN | 1706959 | A | 12/2005 |
| CN | 1901939 | A | 1/2007 |
| CN | 1940087 | A | 4/2007 |
| CN | 101524346 | A | 9/2009 |
| CN | 101970660 | A | 2/2011 |
| CN | 103184297 | A | 7/2013 |
| CN | 103205509 | A | 7/2013 |
| CN | 104131006 | A | 11/2014 |
| CN | 105392363 | A | 3/2016 |
| CN | 110144422 | A | 8/2019 |
| CN | 110157839 | A | 8/2019 |
| CN | 110438092 | A | 11/2019 |
| CN | 110468234 | A | 11/2019 |
| CN | 110982876 | A | 4/2020 |
| CN | 110982942 | A | 4/2020 |
| WO | 01/01129 | A2 | 1/2001 |
| WO | 2005042030 | A1 | 5/2005 |
| WO | 2009153299 | A1 | 12/2009 |

OTHER PUBLICATIONS

PCT Written Opinion of the International Searching Authority, International application No. PCT /CN2020/090054, mailed Dec. 16, 2020.

PCT International Search Report, International application No. PCT /CN2020/090054, mailed Dec. 16, 2020.

Supplementary European Search Report, Application No. EP20923345, Nov. 4, 2022.

Dandan Li et al., Title of the article: Primer design for quantitative real-time PCR for the emerging Coronavirus SARS-CoV-2, Theranostics 2020, vol. 10, pp. 7150-7162, Australia, Jun. 1, 2020.

Victor M Corman et al. Title of the article: (Molecular Diagnosis of )Detection of 2019 novel coronavirus (2019-nCoV) by real-time RT-PCR, Euro. Surveill. 2020, vol. 25(3), Sweden, Jan. 23, 2020.

Daniel K. W. Chu et al., Title of the article: Molecular Diagnosis of a Novel Coronavirus(2019-nCOV)Causing an Outbreak of Pneumonia, American Association for Clinical Chemistry, vol. 66, pp. 549-555, America, Jan. 31, 2020.

Minzhe Shen et al., Title of the item: Recent advances and perspectives of nucleic acid detection for coronavirus Journal of Pharmaceutical Analysis, vol. 10, ppgs 97-101, China, Mar. 1, 2020.

Theresa Cromeans, et al.; A new solid matrix for preservation of viral nucleic acid from clinical specimens at ambient temperature; Journal of Virological Methods; Sep. 11, 2010; p. 1-7; vol. 274; Netherlands.

First Office Action for 202010143226.2; Issued Apr. 17, 2020.

Supplementary European Search Report for EP20923230.5; Issued May 12, 2022.

Long Youmin et al.; Evaluation of Application Performance for a New HBV-DNA Fluorescence Quantitative PCR Diagnostic Kit by Nucleic Acid Ectraction-free Method; Clinical Medicine & Engineering; May 30, 2011; p. 652-653; vol. 18; Guangdong, China.

(Continued)

*Primary Examiner* — Nicole Kinsey White

(74) *Attorney, Agent, or Firm* — Flener IP & Business Law

(57) ABSTRACT

Provided in the present invention is a composition capable of detecting and typing novel coronavirus 2019-nCoV, coronavirus 229E, coronavirus NL63, coronavirus OC43, coronavirus HKU1, coronavirus MERSr-CoV, and coronavirus SARSr-CoV. At the same time, further provided is a kit comprising the composition and a method for detecting and typing coronaviruses. The composition of the present invention in combination with a fluorescent probe method and a melting curve method can perform simultaneous detection and typing of seven coronaviruses in one tube.

17 Claims, 8 Drawing Sheets

Specification includes a Sequence Listing.

(56) References Cited

OTHER PUBLICATIONS

International Search Report for PCT/CN2020/090052; issued Dec. 14, 2020.
Written Opinion of the International Search Authority for PCT/CN2020/090052; issued Dec. 14, 2020.

A

B

C

A

B

C

A

B

C

A

B

C

A

B

C

A

B

C

A

B

C

A

B

C

SEQUENCE LISTING

```
Sequence total quantity: 60
SEQ ID NO: 1            moltype = DNA  length = 20
FEATURE                 Location/Qualifiers
source                  1..20
                        mol_type = other DNA
                        note = Novel coronavirus 2019-nCoV forward primer
                        organism = synthetic construct
SEQUENCE: 1
tgtagcttgt cacaccgttt                                              20

SEQ ID NO: 2            moltype = DNA  length = 23
FEATURE                 Location/Qualifiers
source                  1..23
                        mol_type = other DNA
                        note = Novel coronavirus 2019-nCoV reverse primer
                        organism = synthetic construct
SEQUENCE: 2
attagcataa gcagttgtgg cat                                          23

SEQ ID NO: 3            moltype = DNA  length = 25
FEATURE                 Location/Qualifiers
source                  1..25
                        mol_type = other DNA
                        note = Novel coronavirus 2019-nCoV probe
                        organism = synthetic construct
SEQUENCE: 3
atagtgaacc gccacacatg accat                                        25

SEQ ID NO: 4            moltype = DNA  length = 23
FEATURE                 Location/Qualifiers
source                  1..23
                        mol_type = other DNA
                        note = Coronavirus NL63 forward primer
```

-continued

```
                       organism = synthetic construct
SEQUENCE: 4
gtcttggtaa tcgcaaacgt aat                                          23

SEQ ID NO: 5           moltype = DNA  length = 22
FEATURE                Location/Qualifiers
source                 1..22
                       mol_type = other DNA
                       note = Coronavirus NL63 reverse primer
                       organism = synthetic construct
SEQUENCE: 5
agaatcagaa cgagtgcgag ac                                           22

SEQ ID NO: 6           moltype = DNA  length = 28
FEATURE                Location/Qualifiers
source                 1..28
                       mol_type = other DNA
                       note = Coronavirus NL63 probe
                       organism = synthetic construct
SEQUENCE: 6
ctctctgttg ttgagtttga ggatcgct                                     28

SEQ ID NO: 7           moltype = DNA  length = 25
FEATURE                Location/Qualifiers
source                 1..25
                       mol_type = other DNA
                       note = Coronavirus HKU1 forward primer
                       organism = synthetic construct
SEQUENCE: 7
ttgttagtag tttagttttg gctcg                                        25

SEQ ID NO: 8           moltype = DNA  length = 23
FEATURE                Location/Qualifiers
source                 1..23
                       mol_type = other DNA
                       note = Coronavirus HKU1 reverse primer
                       organism = synthetic construct
SEQUENCE: 8
cgccacacat aactatttca ctc                                          23

SEQ ID NO: 9           moltype = DNA  length = 25
FEATURE                Location/Qualifiers
source                 1..25
                       mol_type = other DNA
                       note = Coronavirus HKU1 probe
                       organism = synthetic construct
SEQUENCE: 9
attctatcgc cttgcgaatg aatgt                                        25

SEQ ID NO: 10          moltype = DNA  length = 19
FEATURE                Location/Qualifiers
source                 1..19
                       mol_type = other DNA
                       note = Coronavirus 229E forward primer
                       organism = synthetic construct
SEQUENCE: 10
aatttgctga gcttgtgcc                                               19

SEQ ID NO: 11          moltype = DNA  length = 24
FEATURE                Location/Qualifiers
source                 1..24
                       mol_type = other DNA
                       note = Coronavirus 229E reverse primer
                       organism = synthetic construct
SEQUENCE: 11
taactcctca agaaacttac ccaa                                         24

SEQ ID NO: 12          moltype = DNA  length = 21
FEATURE                Location/Qualifiers
source                 1..21
                       mol_type = other DNA
                       note = Coronavirus OC43 forward primer
                       organism = synthetic construct
SEQUENCE: 12
aatctactgg gtcgctagca a                                            21

SEQ ID NO: 13          moltype = DNA  length = 21
FEATURE                Location/Qualifiers
source                 1..21
```

```
                         mol_type = other DNA
                         note = Coronavirus OC43 reverse primer
                         organism = synthetic construct
SEQUENCE: 13
tagtcggaat agcctcatcg c                                            21

SEQ ID NO: 14            moltype = DNA  length = 25
FEATURE                  Location/Qualifiers
source                   1..25
                         mol_type = other DNA
                         note = Coronavirus MERSr-CoV forward primer
                         organism = synthetic construct
SEQUENCE: 14
caaaagaaga atcaacagac caaat                                        25

SEQ ID NO: 15            moltype = DNA  length = 21
FEATURE                  Location/Qualifiers
source                   1..21
                         mol_type = other DNA
                         note = Coronavirus MERSr-CoV reverse primer
                         organism = synthetic construct
SEQUENCE: 15
tcattggacc aggctgaaca c                                            21

SEQ ID NO: 16            moltype = DNA  length = 24
FEATURE                  Location/Qualifiers
source                   1..24
                         mol_type = other DNA
                         note = Coronavirus SARSr-CoV forward primer
                         organism = synthetic construct
SEQUENCE: 16
catgcttagg ataatggcct ctct                                         24

SEQ ID NO: 17            moltype = DNA  length = 25
FEATURE                  Location/Qualifiers
source                   1..25
                         mol_type = other DNA
                         note = Coronavirus SARSr-CoV reverse primer
                         organism = synthetic construct
SEQUENCE: 17
acctgtagaa acggtgtgac aagtt                                        25

SEQ ID NO: 18            moltype = DNA  length = 23
FEATURE                  Location/Qualifiers
source                   1..23
                         mol_type = other DNA
                         note = Internal standard forward primer
                         organism = synthetic construct
SEQUENCE: 18
tccatctcac tgcaatgttt tga                                          23

SEQ ID NO: 19            moltype = DNA  length = 23
FEATURE                  Location/Qualifiers
source                   1..23
                         mol_type = other DNA
                         note = Internal standard reverse primer
                         organism = synthetic construct
SEQUENCE: 19
tggaaaaact gcaacaacat cat                                          23

SEQ ID NO: 20            moltype = DNA  length = 23
FEATURE                  Location/Qualifiers
source                   1..23
                         mol_type = other DNA
                         note = Internal standard probe
                         organism = synthetic construct
SEQUENCE: 20
agcaacttct tcaagggccc ggc                                          23

SEQ ID NO: 21            moltype = DNA  length = 19
FEATURE                  Location/Qualifiers
source                   1..19
                         mol_type = other DNA
                         note = Novel coronavirus 2019-nCoV forward primer 2
                         organism = synthetic construct
SEQUENCE: 21
gccccaaggt ttacccaat                                               19

SEQ ID NO: 22            moltype = DNA  length = 20
```

-continued

```
FEATURE                 Location/Qualifiers
source                  1..20
                        mol_type = other DNA
                        note = Novel coronavirus 2019-nCoV reverse primer 2
                        organism = synthetic construct
SEQUENCE: 22
aggtcttcct tgccatgttg                                          20

SEQ ID NO: 23           moltype = DNA  length = 25
FEATURE                 Location/Qualifiers
source                  1..25
                        mol_type = other DNA
                        note = Novel coronavirus 2019-nCoV probe 2
                        organism = synthetic construct
SEQUENCE: 23
actgcgtctt ggttcaccgc tctca                                    25

SEQ ID NO: 24           moltype = DNA  length = 18
FEATURE                 Location/Qualifiers
source                  1..18
                        mol_type = other DNA
                        note = Novel coronavirus 2019-nCoV forward primer 3
                        organism = synthetic construct
SEQUENCE: 24
ggccgcaaat tgcacaat                                            18

SEQ ID NO: 25           moltype = DNA  length = 21
FEATURE                 Location/Qualifiers
source                  1..21
                        mol_type = other DNA
                        note = Novel coronavirus 2019-nCoV reverse primer 3
                        organism = synthetic construct
SEQUENCE: 25
gtgtgacttc catgccaatg c                                        21

SEQ ID NO: 26           moltype = DNA  length = 22
FEATURE                 Location/Qualifiers
source                  1..22
                        mol_type = other DNA
                        note = Novel coronavirus 2019-nCoV probe 3
                        organism = synthetic construct
SEQUENCE: 26
cccccagcgc ttcagcgttc tt                                       22

SEQ ID NO: 27           moltype = DNA  length = 23
FEATURE                 Location/Qualifiers
source                  1..23
                        mol_type = other DNA
                        note = Coronavirus NL63 forward primer 2
                        organism = synthetic construct
SEQUENCE: 27
ctagcagtcg ttcttcaact cgt                                      23

SEQ ID NO: 28           moltype = DNA  length = 20
FEATURE                 Location/Qualifiers
source                  1..20
                        mol_type = other DNA
                        note = Coronavirus NL63 reverse primer 2
                        organism = synthetic construct
SEQUENCE: 28
gccaaagtaa cagcagcaac                                          20

SEQ ID NO: 29           moltype = DNA  length = 30
FEATURE                 Location/Qualifiers
source                  1..30
                        mol_type = other DNA
                        note = Coronavirus NL63 probe 2
                        organism = synthetic construct
SEQUENCE: 29
cgtagcactt caagacaaca gtctcgcact                               30

SEQ ID NO: 30           moltype = DNA  length = 20
FEATURE                 Location/Qualifiers
source                  1..20
                        mol_type = other DNA
                        note = Coronavirus NL63 forward primer 3
                        organism = synthetic construct
SEQUENCE: 30
ttgagtttga ggatcgctct                                          20
```

```
SEQ ID NO: 31           moltype = DNA  length = 23
FEATURE                 Location/Qualifiers
source                  1..23
                        mol_type = other DNA
                        note = Coronavirus NL63 forward primer 3
                        organism = synthetic construct
SEQUENCE: 31
gactgttgtc ttgaagtgct acg                                     23

SEQ ID NO: 32           moltype = DNA  length = 32
FEATURE                 Location/Qualifiers
source                  1..32
                        mol_type = other DNA
                        note = Coronavirus NL63 probe 3
                        organism = synthetic construct
SEQUENCE: 32
actcatctcg tgctagcagt cgttcttcaa ct                           32

SEQ ID NO: 33           moltype = DNA  length = 21
FEATURE                 Location/Qualifiers
source                  1..21
                        mol_type = other DNA
                        note = Coronavirus HKU1 forward primer 2
                        organism = synthetic construct
SEQUENCE: 33
tgcccacgaa ggtatcttct g                                       21

SEQ ID NO: 34           moltype = DNA  length = 17
FEATURE                 Location/Qualifiers
source                  1..17
                        mol_type = other DNA
                        note = Coronavirus HKU1 reverse primer 2
                        organism = synthetic construct
SEQUENCE: 34
ggatcccttg ccgaaac                                            17

SEQ ID NO: 35           moltype = DNA  length = 29
FEATURE                 Location/Qualifiers
source                  1..29
                        mol_type = other DNA
                        note = Coronavirus HKU1 probe 2
                        organism = synthetic construct
SEQUENCE: 35
tcaccaagct gacacttcta ttccctccg                               29

SEQ ID NO: 36           moltype = DNA  length = 21
FEATURE                 Location/Qualifiers
source                  1..21
                        mol_type = other DNA
                        note = Coronavirus HKU1 forward primer 3
                        organism = synthetic construct
SEQUENCE: 36
cccaacccaa attcactgtg t                                       21

SEQ ID NO: 37           moltype = DNA  length = 20
FEATURE                 Location/Qualifiers
source                  1..20
                        mol_type = other DNA
                        note = Coronavirus HKU1 reverse primer 3
                        organism = synthetic construct
SEQUENCE: 37
ggtaatccca gagaaccagg                                         20

SEQ ID NO: 38           moltype = DNA  length = 30
FEATURE                 Location/Qualifiers
source                  1..30
                        mol_type = other DNA
                        note = Coronavirus HKU1 probe 3
                        organism = synthetic construct
SEQUENCE: 38
actcaaccac aaggaaaccc tatcccacat                              30

SEQ ID NO: 39           moltype = DNA  length = 27
FEATURE                 Location/Qualifiers
source                  1..27
                        mol_type = other DNA
                        note = Coronavirus 229E forward primer 2
                        organism = synthetic construct
```

```
SEQUENCE: 39
caacaacatc ctcttcttaa ccctagt                                    27

SEQ ID NO: 40           moltype = DNA  length = 21
FEATURE                 Location/Qualifiers
source                  1..21
                        mol_type = other DNA
                        note = Coronavirus 229E reverse primer 2
                        organism = synthetic construct
SEQUENCE: 40
ttcatcacgc actggttcaa c                                          21

SEQ ID NO: 41           moltype = DNA  length = 26
FEATURE                 Location/Qualifiers
source                  1..26
                        mol_type = other DNA
                        note = Coronavirus 229E forward primer 3
                        organism = synthetic construct
SEQUENCE: 41
gtcacccaag ttgcattttt attatc                                     26

SEQ ID NO: 42           moltype = DNA  length = 19
FEATURE                 Location/Qualifiers
source                  1..19
                        mol_type = other DNA
                        note = Coronavirus 229E reverse primer 3
                        organism = synthetic construct
SEQUENCE: 42
cccagacgac accttcaac                                             19

SEQ ID NO: 43           moltype = DNA  length = 23
FEATURE                 Location/Qualifiers
source                  1..23
                        mol_type = other DNA
                        note = Coronavirus OC43 forward primer 2
                        organism = synthetic construct
SEQUENCE: 43
ctggtacaga cacaacagac gtt                                        23

SEQ ID NO: 44           moltype = DNA  length = 18
FEATURE                 Location/Qualifiers
source                  1..18
                        mol_type = other DNA
                        note = Coronavirus OC43 reverse primer 2
                        organism = synthetic construct
SEQUENCE: 44
accatcgtgg cagcagtt                                              18

SEQ ID NO: 45           moltype = DNA  length = 22
FEATURE                 Location/Qualifiers
source                  1..22
                        mol_type = other DNA
                        note = Coronavirus OC43 forward primer 3
                        organism = synthetic construct
SEQUENCE: 45
gcgatgaggc tattccgact ag                                         22

SEQ ID NO: 46           moltype = DNA  length = 28
FEATURE                 Location/Qualifiers
source                  1..28
                        mol_type = other DNA
                        note = Coronavirus OC43 reverse primer 3
                        organism = synthetic construct
SEQUENCE: 46
accttcctga gccttcaata tagtaacc                                   28

SEQ ID NO: 47           moltype = DNA  length = 19
FEATURE                 Location/Qualifiers
source                  1..19
                        mol_type = other DNA
                        note = Coronavirus MERSr-CoV forward primer 2
                        organism = synthetic construct
SEQUENCE: 47
caactggctc ccaggtggt                                             19

SEQ ID NO: 48           moltype = DNA  length = 20
FEATURE                 Location/Qualifiers
source                  1..20
                        mol_type = other DNA
```

```
                        note = Coronavirus MERSr-CoV reverse primer 2
                        organism = synthetic construct
SEQUENCE: 48
tccttaacag cccggaatgg                                                20

SEQ ID NO: 49           moltype = DNA  length = 19
FEATURE                 Location/Qualifiers
source                  1..19
                        mol_type = other DNA
                        note = Coronavirus MERSr-CoV forward primer 3
                        organism = synthetic construct
SEQUENCE: 49
ggcactgagg acccacgtt                                                 19

SEQ ID NO: 50           moltype = DNA  length = 23
FEATURE                 Location/Qualifiers
source                  1..23
                        mol_type = other DNA
                        note = Coronavirus MERSr-CoV reverse primer 3
                        organism = synthetic construct
SEQUENCE: 50
aattgcgaca tacccataaa agc                                            23

SEQ ID NO: 51           moltype = DNA  length = 20
FEATURE                 Location/Qualifiers
source                  1..20
                        mol_type = other DNA
                        note = Coronavirus SARSr-CoV forward primer 2
                        organism = synthetic construct
SEQUENCE: 51
tggcctctct tgttcttgct                                                20

SEQ ID NO: 52           moltype = DNA  length = 21
FEATURE                 Location/Qualifiers
source                  1..21
                        mol_type = other DNA
                        note = Coronavirus SARSr-CoV reverse primer 2
                        organism = synthetic construct
SEQUENCE: 52
ctgatgatgt tccacctggt t                                              21

SEQ ID NO: 53           moltype = DNA  length = 20
FEATURE                 Location/Qualifiers
source                  1..20
                        mol_type = other DNA
                        note = Coronavirus SARSr-CoV forward primer 3
                        organism = synthetic construct
SEQUENCE: 53
aatgtgacag agccatgcct                                                20

SEQ ID NO: 54           moltype = DNA  length = 25
FEATURE                 Location/Qualifiers
source                  1..25
                        mol_type = other DNA
                        note = Coronavirus SARSr-CoV reverse primer 3
                        organism = synthetic construct
SEQUENCE: 54
catagcactt gctgtaactt gtcac                                          25

SEQ ID NO: 55           moltype = DNA  length = 17
FEATURE                 Location/Qualifiers
source                  1..17
                        mol_type = other DNA
                        note = Internal standard forward primer 2
                        organism = synthetic construct
SEQUENCE: 55
gccaagtgtg agggctg                                                   17

SEQ ID NO: 56           moltype = DNA  length = 24
FEATURE                 Location/Qualifiers
source                  1..24
                        mol_type = other DNA
                        note = Internal standard reverse primer 2
                        organism = synthetic construct
SEQUENCE: 56
ggctgatgaa ctataaaagg gaag                                           24

SEQ ID NO: 57           moltype = DNA  length = 26
FEATURE                 Location/Qualifiers
```

-continued

```
source                  1..26
                        mol_type = other DNA
                        note = Internal standard probe 2
                        organism = synthetic construct
SEQUENCE: 57
aatgccccag tctctgtcag cactcc                                       26

SEQ ID NO: 58           moltype = DNA  length = 19
FEATURE                 Location/Qualifiers
source                  1..19
                        mol_type = other DNA
                        note = Internal standard forward primer 3
                        organism = synthetic construct
SEQUENCE: 58
ctcggatcca tctcactgc                                               19

SEQ ID NO: 59           moltype = DNA  length = 24
FEATURE                 Location/Qualifiers
source                  1..24
                        mol_type = other DNA
                        note = Internal standard reverse primer 3
                        organism = synthetic construct
SEQUENCE: 59
ttggaaaaac tgcaacaaca tcat                                         24

SEQ ID NO: 60           moltype = DNA  length = 22
FEATURE                 Location/Qualifiers
source                  1..22
                        mol_type = other DNA
                        note = Internal standard probe 3
                        organism = synthetic construct
SEQUENCE: 60
caacttcttc aagggcccgg ct                                           22
```

COMPOSITION, KIT, AND METHOD FOR DETECTING AND TYPING CORONAVIRUSES

CROSS-REFERENCE TO RELATED APPLICATIONS

This application is a continuation of International Application No. PCT/CN2020/090054, filed on May 13, 2020, which claims priority to Chinese Patent Application No. 202010136909.5, filed on Mar. 2, 2020. The disclosures of the aforementioned applications are hereby incorporated by reference in their entireties.

REFERENCE TO AN ELECTRONIC SEQUENCE LISTING

The contents of the electronic sequence listing (CU693 SequenceListing.xml; Size: 65,593 bytes; and Date of Creation: Aug. 19, 2022) is herein incorporated by reference in its entirety.

TECHNICAL FIELD

The present invention relates to the field of molecular biological detection, more specifically, to the field of detection of coronaviruses. More specifically, the present invention is capable of detecting and typing novel coronavirus 2019-nCoV, coronavirus 229E, coronavirus NL63, coronavirus OC43, coronavirus HKU1, coronavirus MERSr-CoV, and coronavirus SARSr-CoV.

BACKGROUND

Coronaviruses are nonsegmented, single stranded and positive-stranded RNA viruses, which belong to the Orthocoronavirinae subfamily of the Coronaviridae family of the order Nidovirales. According to serotypes and genome characteristics, the coronavirus subfamily is divided into four genera: α, β, γ, and δ, and can infect many animal species, including humans, bats, dogs, pigs, mice, birds, cattle, whales, horses, goats, monkeys, etc. There are six coronaviruses known to infect humans, including 229E and NL63 of the genus α, OC43 and HKU1 of the genus β, the Middle East respiratory syndrome-related coronavirus (MERSr-CoV), and the severe acute respiratory syndrome-related coronavirus (SARSr-CoV). In December 2019, an unexplained pneumonia infection event occurred in Wuhan, Hubei, and a new type of coronavirus belonging to the genus (3 was isolated from the lower respiratory tract of patients. Subsequently, the World Health Organization named the virus "2019 Novel Coronavirus (2019-nCoV)."

The novel coronavirus is a novel coronavirus of the genus (3, which has an envelope and round or oval particles, often pleomorphic, with a diameter of 60-140 nm. The genetic characteristics thereof are significantly different from those of SARSr-CoV and MERSr-CoV. According to the latest research results of researcher Shi Zhengli from the Wuhan Institute of Virology, 2019-nCoV is highly similar to RaTG13, a bat coronavirus strain previously isolated from Chinese rufous horseshoe bats in her laboratory, with an overall genomic similarity of 96.2%. In addition, studies have shown that 2019-nCoV is 85% or more homologous to bat SARS-like coronaviruses (bat-SL-CoVZC45 and bat-SL-CoVZXC21).

Among the seven coronaviruses that can infect humans, coronavirus 229E, coronavirus NL63, coronavirus OC43, and coronavirus HKU1 are common respiratory infectious viruses, which cause mild cases after infecting people and usually do not induce severe illnesses. However, novel coronavirus 2019-nCoV, coronavirus MERSr-CoV, and coronavirus SARSr-CoV infections will cause very serious infection symptoms in patients, and are highly likely to develop into severe illnesses. If various coronaviruses can be clearly typed in a single test, subsequent diagnosis and treatment measures will be greatly facilitated, to achieve precise treatment, prevention and control, especially for the highly contagious and harmful novel coronavirus 2019-nCoV, coronavirus MERSr-CoV, and coronavirus SARSr-CoV, making it possible to control the source of infection in a timely manner and block virus pandemics and outbreaks.

Therefore, there is a need in the art for a related product that can perform simultaneous and rapid identification and typing of multiple coronaviruses.

SUMMARY

In view of this, provided in the present invention is a composition capable of detecting and typing coronaviruses, the composition including:

a first group:

- a novel coronavirus 2019-nCoV forward primer as shown in SEQ ID NO: 1, a novel coronavirus 2019-nCoV reverse primer as shown in SEQ ID NO: 2, and a novel coronavirus 2019-nCoV probe as shown in SEQ ID NO: 3;
- a coronavirus NL63 forward primer as shown in SEQ ID NO: 4, a coronavirus NL63 reverse primer as shown in SEQ ID NO: 5, and a coronavirus NL63 probe as shown in SEQ ID NO: 6;
- a coronavirus HKU1 forward primer as shown in SEQ ID NO: 7, a coronavirus HKU1 reverse primer as shown in SEQ ID NO: 8, and a coronavirus HKU1 probe as shown in SEQ ID NO: 9; and a second group:

- a coronavirus 229E forward primer as shown in SEQ ID NO: 10 and a coronavirus 229E reverse primer as shown in SEQ ID NO: 11;
- a coronavirus OC43 forward primer as shown in SEQ ID NO: 12 and a coronavirus OC43 reverse primer as shown in SEQ ID NO: 13;
- a coronavirus MERSr-CoV forward primer as shown in SEQ ID NO: 14 and a coronavirus MERSr-CoV reverse primer as shown in SEQ ID NO: 15; and
- a coronavirus SARSr-CoV forward primer as shown in SEQ ID NO: 16 and a coronavirus SARSr-CoV reverse primer as shown in SEQ ID NO: 17, wherein fluorescent groups in the first group are different from one another, and fluorescent groups in the second group are different from one another.

The coronaviruses includes: novel coronavirus 2019-nCoV, coronavirus 229E, coronavirus NL63, coronavirus OC43, coronavirus HKU1, coronavirus MERSr-CoV, and coronavirus SARSr-CoV.

Using the composition of the present invention in combination with a fluorescent probe method and a melting curve method, it is possible to use one tube to perform simultaneous detection and typing of seven coronaviruses in one test, achieving low costs, high throughput, and less time consumption. The present invention enables information of eight targets to be given by one tube in a single test, greatly improving the detection efficiency, and the operations are simple and convenient, and a result reading process can be determinated according to an amplification curve and a CT value. The whole detection process is carried out under single-tube closed conditions, avoiding false positives and environmental contamination caused by crossover between samples.

In the present invention, the fluorescent reporter group may be selected from FAM, HEX, ROX, VIC, CY5, 5-TAMRA, TET, CY3, and JOE, but is not limited thereto.

In one specific embodiment, the fluorescent reporter group of the novel coronavirus 2019-nCoV probe as shown in SEQ ID NO: 3 is FAM; the fluorescent reporter group of the coronavirus NL63 probe as shown in SEQ ID NO: 6 is HEX; and the fluorescent reporter group of the coronavirus HKU1 probe as shown in SEQ ID NO: 9 is ROX.

In one specific embodiment, the fluorescent reporter group of the coronavirus 229E forward primer as shown in SEQ ID NO: 10 is FAM; the fluorescent reporter group of the coronavirus OC43 forward primer as shown in SEQ ID NO: 12 is HEX; the fluorescent reporter group of the coronavirus MERSr-CoV forward primer as shown in SEQ ID NO: 14 is ROX; and the fluorescent reporter group for the coronavirus SARSr-CoV as shown in SEQ ID NO: 16 is CY5.

In one embodiment, the components of the composition of the present invention are in the same package.

Further, the composition further includes: an internal standard forward primer as shown in SEQ ID NO: 18, an internal standard reverse primer as shown in SEQ ID NO: 19, and an internal standard probe as shown in SEQ ID NO: 20.

In one specific embodiment, a fluorescent reporter group of the internal standard probe as shown in SEQ ID NO: 20 is CY5.

Further, the amount of the primer in the composition is 50-150 nM, and the amount of the probe in the composition is 25-75 nM.

In a second aspect, provided in the present invention is a use of the composition of the present invention in the preparation of a kit for detecting and typing coronaviruses.

The coronavirus includes: novel coronavirus 2019-nCoV, coronavirus 229E, coronavirus NL63, coronavirus OC43, coronavirus HKU1, coronavirus MERSr-CoV, and coronavirus SARSr-CoV.

In a third aspect, provided in the present invention is a kit for detecting and typing coronaviruses, the kit including the composition of the present invention.

Further, the kit further includes at least one of a nucleic acid release reagent, a dNTP, a reverse transcriptase, a DNA polymerase, a PCR buffer, and $Mg^{2+}$.

Further, the amount of the primer in the composition is 50-150 nM, the amount of the probe in the composition is 25-75 nM, and the amount of the dNTP is 0.2-0.3 mM.

Further, the concentration of the reverse transcriptase is 5 U/μL to 15 U/μL, and for example, the reverse transcriptase may be a murine leukemia reverse transcriptase (MMLV). The concentration of the DNA polymerase is 5 U/μL to 15 U/μL, and for example, the DNA polymerase may be a Taq enzyme.

In one specific embodiment, in addition to the above composition of the present invention, the kit further includes the following components and amounts:

| Component | Volume/concentration in each reaction |
|---|---|
| $Mg^{2+}$ | 4 mM |
| dNTPs (100 mM) | 0.25 mM |
| MMLV (10 U/μL) | 10 U |
| Taq enzyme (5 U/μL) | 5 U |
| SEQ ID NOs: 1-16 | 100 nM |
| SEQ ID NOs: 17-20 | 50 nM |
| PCR buffer (1.5x) | Make up to 50 μL |

In a fourth aspect, a method for detecting and typing coronaviruses is provided, the method including the steps of:

1) releasing a nucleic acid of a testing sample;
2) performing, by using the above composition of the present invention or the above kit of the present invention, a fluorescent quantitative PCR on the nucleic acids obtained in step 1); and
3) obtaining and analyzing the results.

In the present invention, the sample for detection may be a throat swab, sputum, a bronchoalveolar lavage fluid, blood, etc., but is not limited thereto.

Further, reaction conditions of the fluorescent quantitative PCR are as follows:

| Step | Temperature | Time | Number of cycles |
|---|---|---|---|
| Reverse transcription | 50° C. | 25-35 minutes | 1 |
| Pre-denaturation | 94° C. | 2-10 minutes | 1 |
| Denaturation | 94° C. | 10-20 seconds | 45-50 |
| Annealing | 60° C. | 20-40 seconds | |
| Melting curve analysis | 50° C. to 95° C. | Fluorescence is collected every 0.5° C. rise | 1 |

In a variant of the present invention, optionally, the novel coronavirus 2019-nCoV forward primer may be as shown in SEQ ID NO: 24, the novel coronavirus 2019-nCoV reverse primer may be as shown in SEQ ID NO: 25, and the novel coronavirus 2019-nCoV probe may be shown as SEQ ID NO: 26; the coronavirus NL63 forward primer may be as shown in SEQ ID NO: 30, the coronavirus NL63 reverse primer may be as shown in SEQ ID NO: 31, and the coronavirus NL63 probe may be as shown in SEQ ID NO: 32; the coronavirus HKU1 forward primer may be as shown in SEQ ID NO: 36, the coronavirus HKU1 reverse primer may be as shown in SEQ ID NO: 37, and the coronavirus HKU1 probe may be as shown in SEQ ID NO: 38; the coronavirus 229E forward primer may be as shown in SEQ ID NO: 39, and the coronavirus 229E reverse primer may be as shown in SEQ ID NO: 40; the coronavirus OC43 forward primer may be as shown in SEQ ID NO: 45, and the coronavirus OC43 reverse primer may be as shown in SEQ ID NO: 46; the coronavirus MERSr-CoV forward primer may be as shown in SEQ ID NO: 49, and the coronavirus MERSr-CoV reverse primer may be as shown in SEQ ID NO: 50; and/or the coronavirus SARSr-CoV forward primer may be as shown in SEQ ID NO: 51, and the SARSr-CoV reverse primer may be as shown in SEQ ID NO: 52.

DETAILED DESCRIPTION OF EMBODIMENTS

Figure 1:
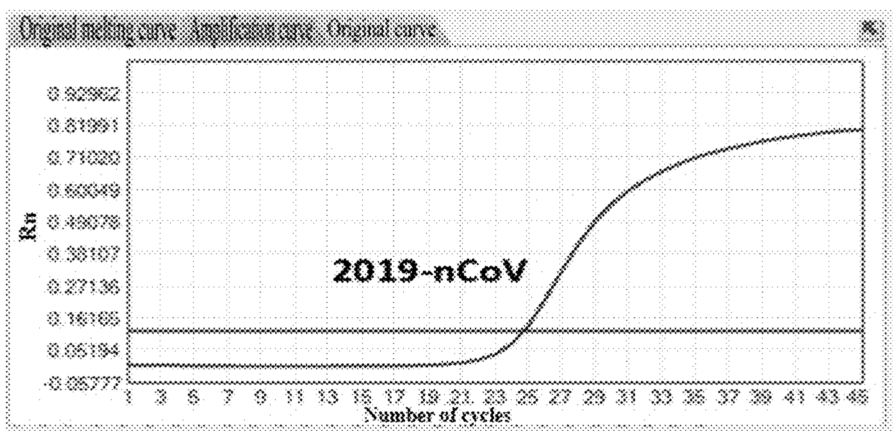
FIG. 1: A is an amplification curve diagram of the composition in Table 1 of the present invention for detecting coronavirus 2019-nCoV; B is an amplification curve diagram of the composition in Table 2 of the present invention for detecting coronavirus 2019-nCoV; C is an amplification curve diagram of the composition in Table 3 of the present invention for detecting coronavirus 2019-nCoV.
Figure 1:
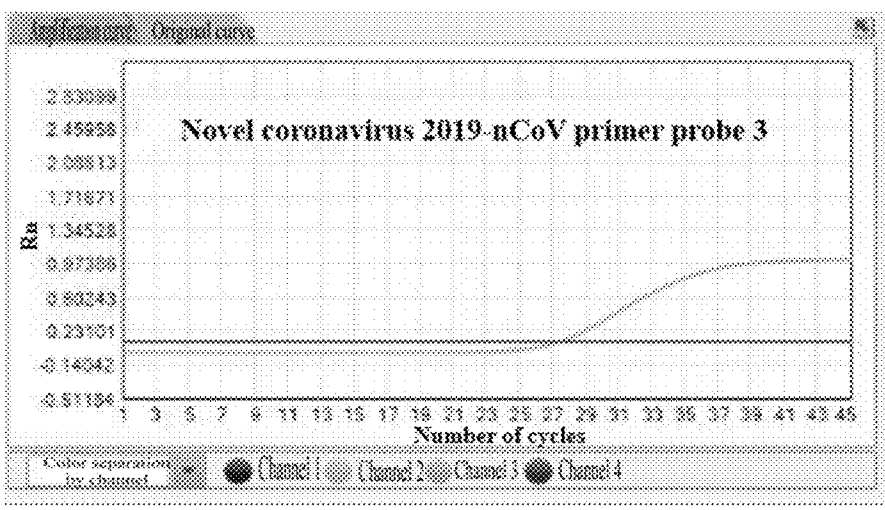
Figure 1:
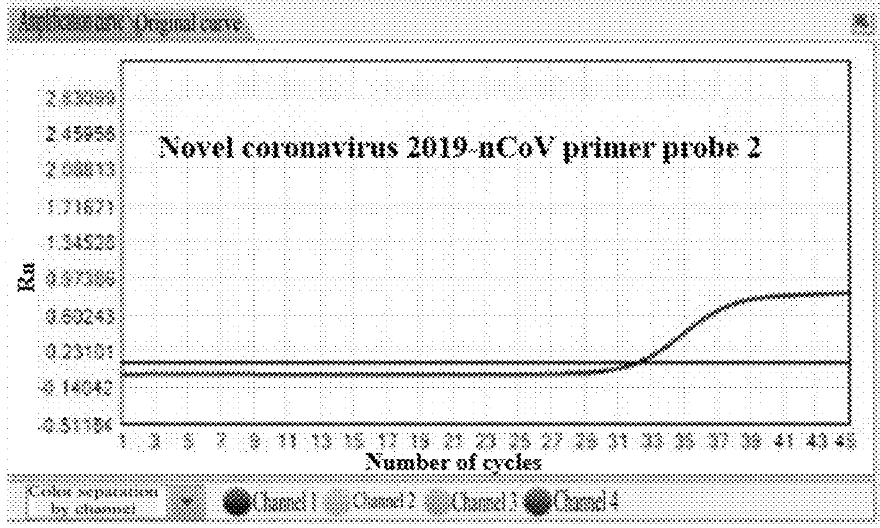

The present invention will be described in detail below with reference to specific embodiments and examples, and the advantages and various effects of the present invention will be more clearly presented therefrom. It should be understood by those skilled in the art that these specific embodiments and examples are intended to illustrate the present invention, rather than to limit the present invention.

Example 1

Primers and Probes Used in the Present Invention

The primers and probes used in the present invention are shown in Tables 1-3 below:

TABLE 1

| | |
|---|---|
| Novel coronavirus 2019-nCoV forward primer (SEQ ID NO: 1) | TGTAGCTTGTCACACCGTTT |
| Novel coronavirus 2019-nCoV reverse primer (SEQ ID NO: 2) | ATTAGCATAAGCAGTTGTGGCAT |
| Novel coronavirus 2019-nCoV probe (SEQ ID NO: 3) | ATAGTGAACCGCCACACATGACCAT |
| Coronavirus NL63 forward primer (SEQ ID NO: 4) | GTCTTGGTAATCGCAAACGTAAT |
| Coronavirus NL63 reverse primer (SEQ ID NO: 5) | AGAATCAGAACGAGTGCGAGAC |
| Coronavirus NL63 probe (SEQ ID NO: 6) | CTCTCTGTTGTTGAGTTTGAGGATCGCT |
| Coronavirus HKU1 forward primer (SEQ ID NO: 7) | TTGTTAGTAGTTTAGTTTTGGCTCG |
| Coronavirus HKU1 reverse primer (SEQ ID NO: 8) | CGCCACACATAACTATTTCACTC |
| Coronavirus HKU1 probe (SEQ ID NO: 9) | ATTCTATCGCCTTGCGAATGAATGT |
| Coronavirus 229E forward primer (SEQ ID NO: 10) | AATTTGCTGAGCTTGTGCC |
| Coronavirus 229E reverse primer (SEQ ID NO: 11) | TAACTCCTCAAGAAACTTACCCAA |
| Coronavirus OC43 forward primer (SEQ ID NO: 12) | AATCTACTGGGTCGCTAGCAA |
| Coronavirus OC43 reverse primer (SEQ ID NO: 13) | TAGTCGGAATAGCCTCATCGC |

TABLE 1-continued

| | |
|---|---|
| Coronavirus MERSr-CoV forward primer (SEQ ID NO: 14) | CAAAAGAAGAATCAACAGACCAAAT |
| Coronavirus MERSr-CoV reverse primer (SEQ ID NO: 15) | TCATTGGACCAGGCTGAACAC |
| Coronavirus SARSr-CoV forward primer (SEQ ID NO: 16) | CATGCTTAGGATAATGGCCTCTCT |
| Coronavirus SARSr-CoV reverse primer (SEQ ID NO: 17) | ACCTGTAGAAACGGTGTGACAAGTT |
| Internal standard forward primer (SEQ ID NO: 18) | TCCATCTCACTGCAATGTTTTGA |
| Internal standard reverse primer (SEQ ID NO: 19) | TGGAAAAACTGCAACAACATCAT |
| Internal standard probe (SEQ ID NO: 20) | AGCAACTTCTTCAAGGGCCCGGC |

TABLE 2

| | |
|---|---|
| Novel coronavirus 2019-nCoV forward primer 3 (SEQ ID NO: 24) | GGCCGCAAATTGCACAAT |
| Novel coronavirus 2019-nCoV reverse primer 3 (SEQ ID NO: 25) | GTGTGACTTCCATGCCAATGC |
| Novel coronavirus 2019-nCoV probe 3 (SEQ ID NO: 26) | CCCCCAGCGCTTCAGCGTTCTT |
| Coronavirus NL63 forward primer 3 (SEQ ID NO: 30) | TTGAGTTTGAGGATCGCTCT |
| Coronavirus NL63 forward primer 3 (SEQ ID NO: 31) | GACTGTTGTCTTGAAGTGCTACG |
| Coronavirus NL63 probe 3 (SEQ ID NO: 32) | ACTCATCTCGTGCTAGCAGTCGTTCT TCAACT |
| Coronavirus HKU1 forward primer 3 (SEQ ID NO: 36) | CCCAACCCAAATTCACTGTGT |
| Coronavirus HKU1 reverse primer 3 (SEQ ID NO: 37) | GGTAATCCCAGAGAACCAGG |
| Coronavirus HKU1 probe 3 (SEQ ID NO: 38) | ACTCAACCACAAGGAAACCCTATCCC ACAT |
| Coronavirus 229E forward primer 2 (SEQ ID NO: 39) | CAACAACATCCTCTTCTTAACCCTAG T |
| Coronavirus 229E reverse primer 2 (SEQ ID NO: 40) | TTCATCACGCACTGGTTCAAC |
| Coronavirus OC43 forward primer 3 (SEQ ID NO: 45) | GCGATGAGGCTATTCCGACTAG |
| Coronavirus OC43 reverse primer 3 (SEQ ID NO: 46) | ACCTTCCTGAGCCTTCAATATAGTAA CC |
| Coronavirus MERSr-CoV forward primer 3 (SEQ ID NO: 49) | GGCACTGAGGACCCACGTT |
| Coronavirus MERSr-CoV reverse primer 3 (SEQ ID NO: 50) | AATTGCGACATACCCATAAAAGC |
| Coronavirus SARSr-CoV forward primer 2 (SEQ ID NO: 51) | TGGCCTCTCTTGTTCTTGCT |
| Coronavirus SARSr-CoV reverse primer 2 (SEQ ID NO: 52) | CTGATGATGTTCCACCTGGTT |
| Internal standard forward primer 2 (SEQ ID NO: 55) | GCCAAGTGTGAGGGCTG |

TABLE 2-continued

| | |
|---|---|
| Internal standard reverse primer 2 (SEQ ID NO: 56) | GGCTGATGAACTATAAAAGGGAAG |
| Internal standard probe 2 (SEQ ID NO: 57) | AATGCCCCAGTCTCTGTCAGCACTCC |

TABLE 3

| | |
|---|---|
| Novel coronavirus 2019-nCoV forward primer 2 (SEQ ID NO: 21) | GCCCCAAGGTTTACCCAAT |
| Novel coronavirus 2019-nCoV reverse primer 2 (SEQ ID NO: 22) | AGGTCTTCCTTGCCATGTTG |
| Novel coronavirus 2019-nCoV probe 2 (SEQ ID NO: 23) | ACTGCGTCTTGGTTCACCGCTCTCA |
| Coronavirus NL63 forward primer 2 (SEQ ID NO: 27) | CTAGCAGTCGTTCTTCAACTCGT |
| Coronavirus NL63 reverse primer 2 (SEQ ID NO: 28) | GCCAAAGTAACAGCAGCAAC |
| Coronavirus NL63 probe 2 (SEQ ID NO: 29) | CGTAGCACTTCAAGACAACAGTCTCGC ACT |
| Coronavirus HKU1 forward primer 2 (SEQ ID NO: 33) | TGCCCACGAAGGTATCTTCTG |
| Coronavirus HKU1 reverse primer 2 (SEQ ID NO: 34) | GGATCCCTTGCCGAAAC |
| Coronavirus HKU1 probe 2 (SEQ ID NO: 35) | TCACCAAGCTGACACTTCTATTCCCTC CG |
| Coronavirus 229E forward primer 3 (SEQ ID NO: 41) | GTCACCCAAGTTGCATTTTTATTATC |
| Coronavirus 229E reverse primer 3 (SEQ ID NO: 42) | CCCAGACGACACCTTCAAC |
| Coronavirus OC43 forward primer 2 (SEQ ID NO: 43) | CTGGTACAGACACAACAGACGTT |
| Coronavirus OC43 reverse primer 2 (SEQ ID NO: 44) | ACCATCGTGGCAGCAGTT |
| Coronavirus MERSr-CoV forward primer 2 (SEQ ID NO: 47) | CAACTGGCTCCCAGGTGGT |
| Coronavirus MERSr-CoV reverse primer 2 (SEQ ID NO: 48) | TCCTTAACAGCCCGGAATGG |
| Coronavirus SARSr-CoV forward primer 3 (SEQ ID NO: 53) | AATGTGACAGAGCCATGCCT |
| Coronavirus SARSr-CoV reverse primer 3 (SEQ ID NO: 54) | CATAGCACTTGCTGTAACTTGTCAC |
| Internal standard forward primer 3 (SEQ ID NO: 58) | CTCGGATCCATCTCACTGC |
| Internal standard reverse primer 3 (SEQ ID NO: 59) | TTGGAAAAACTGCAACAACATCAT |
| Internal standard probe 3 (SEQ ID NO: 60) | CAACTTCTTCAAGGGCCCGGCT |

Among them, a fluorescent reporter group of the novel coronavirus 2019-nCoV probe was FAM; a fluorescent reporter group of the coronavirus NL63 probe was HEX; a fluorescent reporter group of the coronavirus HKU1 probe was ROX, and the 3'-end of the probes further had a BHQ1 or BHQ2 quencher group.

A fluorescent reporter group of the coronavirus 229E forward primer was FAM; a fluorescent reporter group of the coronavirus OC43 forward primer was HEX; a fluorescent reporter group of the coronavirus MERSr-CoV forward primer was ROX; and a fluorescent reporter group of the coronavirus SARSr-CoV was CY5.

Example 2

Method for Detecting and Typing Coronaviruses

A testing sample of the present invention was a throat swab, sputum, a bronchoalveolar lavage fluid, or blood. A magnetic bead method was used to extract a viral nucleic acid, and the following operations were performed in a sample processing room:

2.1 An appropriate number of 1.5-mL sterilized centrifuge tubes were taken, and labeled as a negative control, a positive control, and a testing sample, respectively. 300 μL of an RNA extraction solution 1 was added to each tube.

2.2 200 μL of the testing sample or the negative control or the positive control was added to each tube. The tube was covered with a cap, and shaken for 10 seconds for through mixing, and subjected to instant centrifugation.

2.3 100 μL of an RNA extraction solution 2-mix was added to each tube (sucked up after sufficient mixing), and the tube was shaken for 10 seconds for through mixing, and left to stand for 10 minutes at room temperature.

2.4 After instant centrifugation, the centrifuge tubes were placed on a separator, and the solution was slowly sucked out after 3 minutes (be careful not to touch a brown substance adhered to the tube wall).

2.5 600 μL of an RNA extraction solution 3 and 200 μL of an RNA extraction solution 4 were added to each tube, and the tube was shaken for 5 seconds for through mixing and subjected to instant centrifugation, and then the centrifuge tube was placed on the separator again.

2.6 After about 3 minutes, the supernatant separated into two layers. A pipette tip was inserted into the bottom of the centrifuge tube, the liquid was slowly sucked up from the bottom completely and discarded. The tube was left to stand for 1 minute and then the residual liquid at the bottom of the tube was completely sucked up and discarded.

2.7 50 μL of PCR-mix was added to each tube, and a pipette tip was used to suck up the PCR-mix to elute the brown residue adhered to the wall of the centrifuge tube. The operation was repeated several times to elute the residue as completely as possible, and then all the eluted brown mixture was transferred to a 0.2-mL PCR reaction tube, and the tube was covered with a cap and transferred to an amplification detecting zone.

The real-time fluorescent PCR reaction system was configured as follows:

| Component | Volume/concentration in each reaction |
|---|---|
| $Mg^{2+}$ | 4 mM |
| dNTPs (100 mM) | 0.25 mM |
| MMLV (10 U/μL) | 10 U |
| Taq enzyme (5 U/μL) | 5 U |
| SEQ ID NOs: 1-16 | 100 nM |
| SEQ ID NOs: 17-20 | 50 nM |
| PCR buffer (1.5x) | Make up to 50 μL |

The PCR amplification program was set up as follows:

| Step | Temperature | Time | Number of cycles |
|---|---|---|---|
| Reverse transcription | 50° C. | 30 minutes | 1 |
| Pre-denaturation | 94° C. | 5 minutes | 1 |
| Denaturation | 94° C. | 15 seconds | 45 |
| Annealing | 60° C. | 30 seconds | |
| Melting curve analysis | 50° C. to 95° C. | Fluorescence is collected every 0.5° C. rise. | 1 |

Result Analysis:

1) Target detection signals were FAM, HEX (or VIC), ROX, and CY5, and an internal reference detection signal was CY5.

2) Baseline setting: The baseline was generally set to 3-15 cycles, which specifically may be adjusted according to actual situations. The adjustment principle was to select a region where a fluorescence signal is relatively stable before exponential amplification, a starting point (Start) avoiding signal fluctuation in an initial stage of fluorescence collection, and an ending point (End) being less by 1-2 cycles than the Ct of a sample showing earliest exponential amplification. Threshold setting: the setting principle was to make a threshold line just exceed the highest point of a normal negative control.

3) It was first analyzed whether an amplification curve for the internal standard is detected in the CY5 channel and Ct≤39, and if so, it indicated that the current test was effective, and subsequent analysis continued to be carried out:

A) if a typical S-shaped amplification curve was detected in the FAM channel and Ct<39, it indicated that the novel coronavirus 2019-nCoV detection result was positive; if a characteristic peak of Tm (69.5±1.0° C.) was detected in the FAM channel, it indicated that the coronavirus 229E detection result was positive;

B) if a typical S-shaped amplification curve was detected in the HEX channel and Ct<40, it indicated that the coronavirus NL63 detection result was positive; if a characteristic peak of Tm (67.0±1.0° C.) was detected in the HEX channel, it indicated that the coronavirus OC43 was positive;

C) if a typical S-shaped amplification curve was detected in the ROX channel and Ct<40, it indicated that the coronavirus HKU1 detection result was positive; if a characteristic peak of Tm (70.5±1.0° C.) was detected in the ROX channel, it indicated that the coronavirus MERSr-CoV detection result was positive; and D) if a characteristic peak of Tm (68.0±1.0° C.) was detected in the CY5 channel, it indicated that the coronavirus SARSr-CoV detection result was positive.

4) If a Ct for the internal standard was not detected in the CY5 channel or Ct>39, it indicated that the concentration of the testing sample was excessively low or there was an interfering substance that inhibited the reaction, and the experiment needed to be re-prepared.

Figure 2:
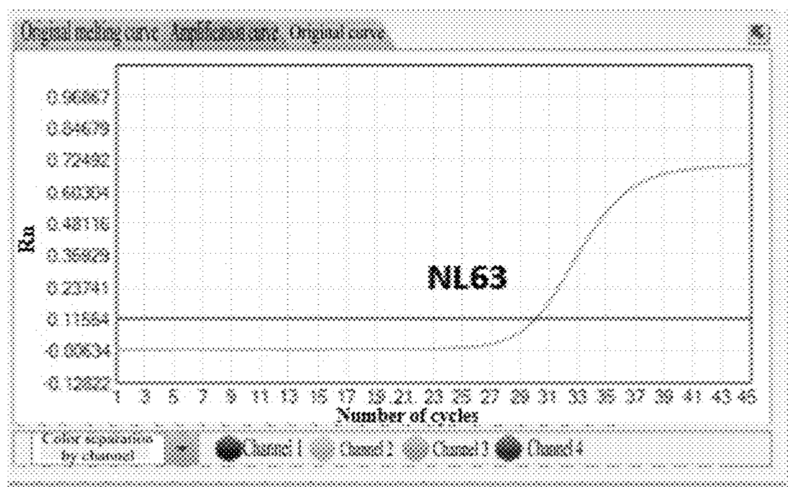
FIG. 2: A is an amplification curve diagram of the composition in Table 1 of the present invention for detecting coronavirus NL63; B is an amplification curve diagram of the composition in Table 2 of the present invention for detecting coronavirus NL63; C is an amplification curve diagram of the composition in Table 3 of the present invention for detecting coronavirus NL63.
Figure 2:
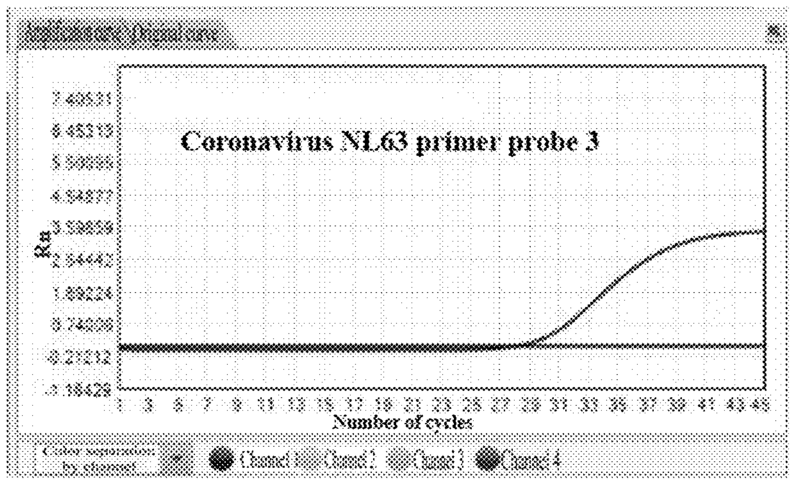
Figure 2:
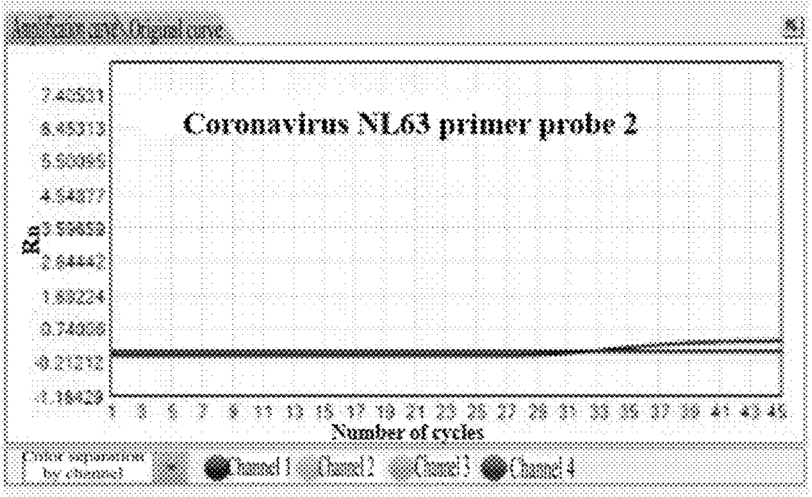
Figure 3:
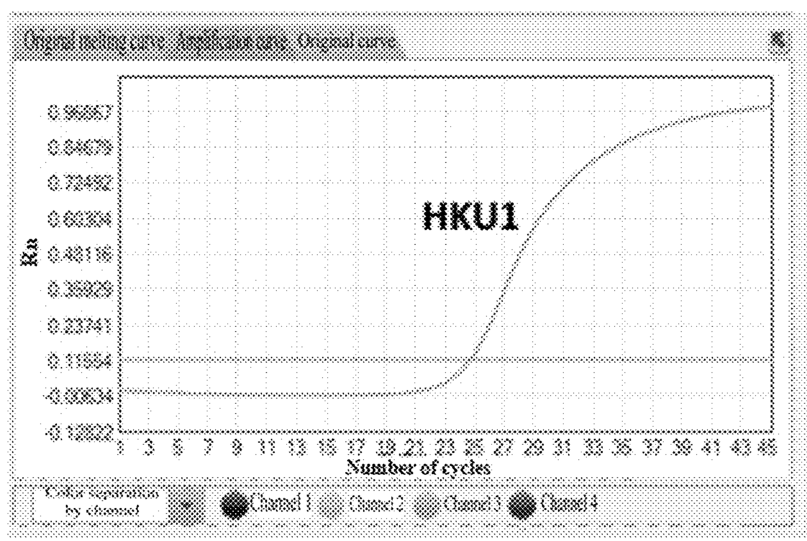
FIG. 3: A is an amplification curve diagram of the composition in Table 1 of the present invention for detecting coronavirus HKU1; B is an amplification curve diagram of the composition in Table 2 of the present invention for detecting coronavirus HKU1; C is an amplification curve diagram of the composition in Table 3 of the present invention for detecting coronavirus HKU1.
Figure 3:
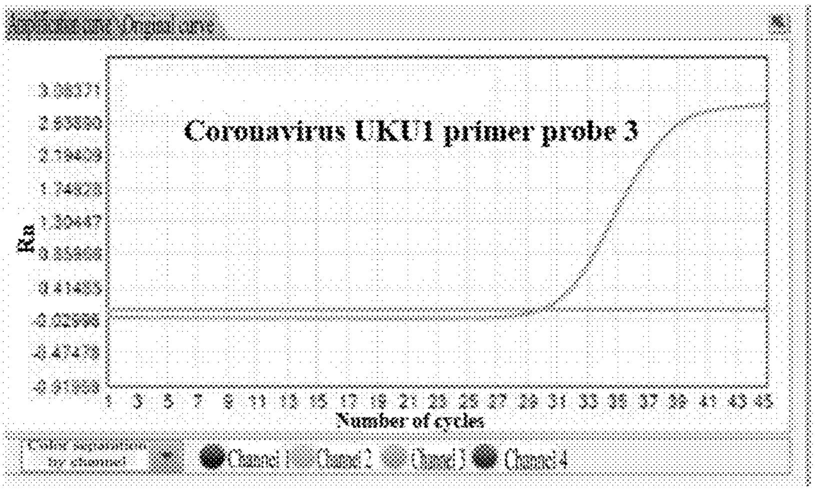
Figure 3:
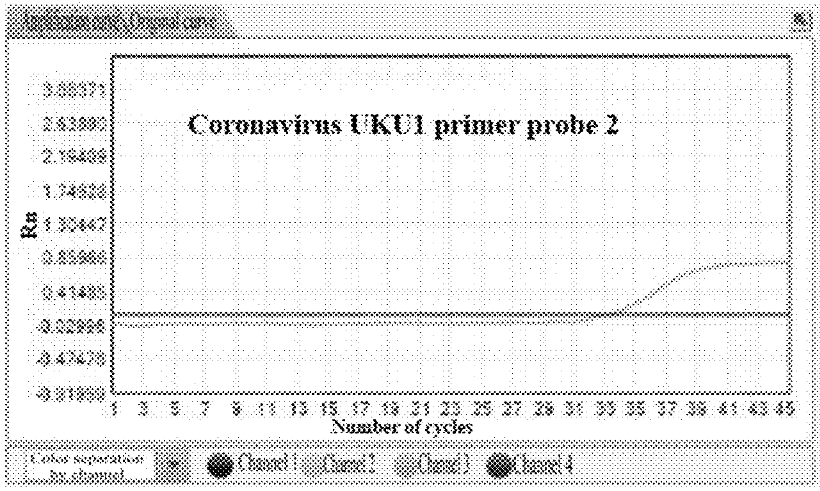
Figure 4:
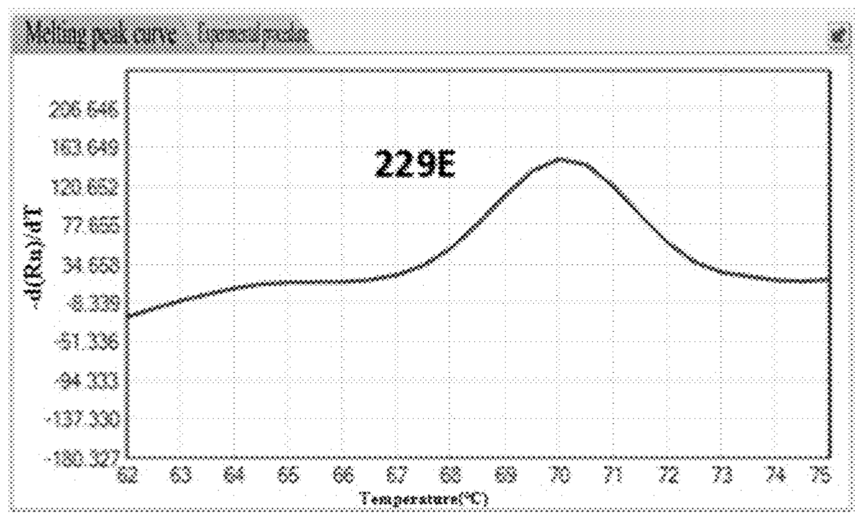
FIG. 4: A is a melting curve diagram of the composition in Table 1 for detecting coronavirus 229E; B is a melting curve diagram of the composition in Table 2 of the present invention for detecting coronavirus 229E; C is a melting curve diagram of the composition in Table 3 of the present invention for detecting coronavirus 229E.
Figure 4:
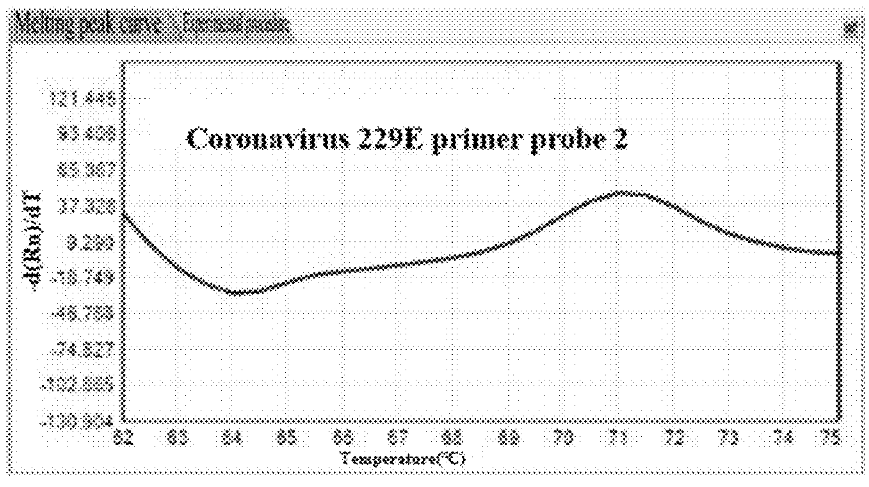
Figure 4:
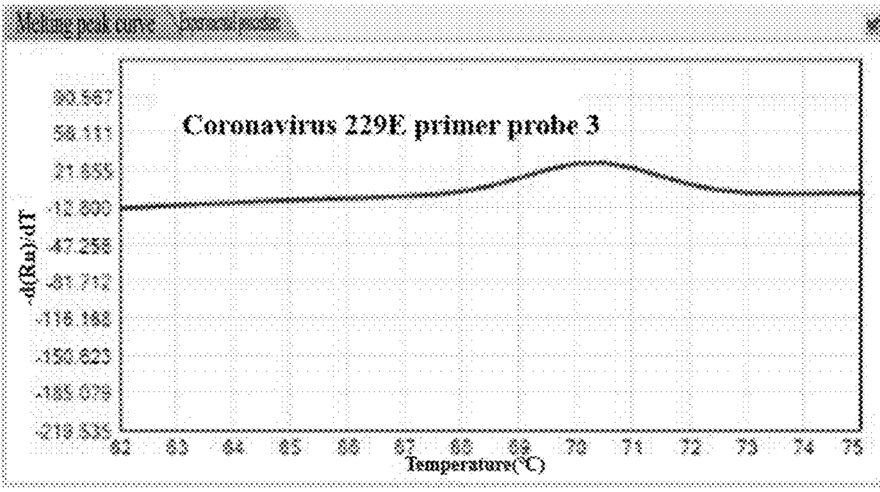
Figure 5:
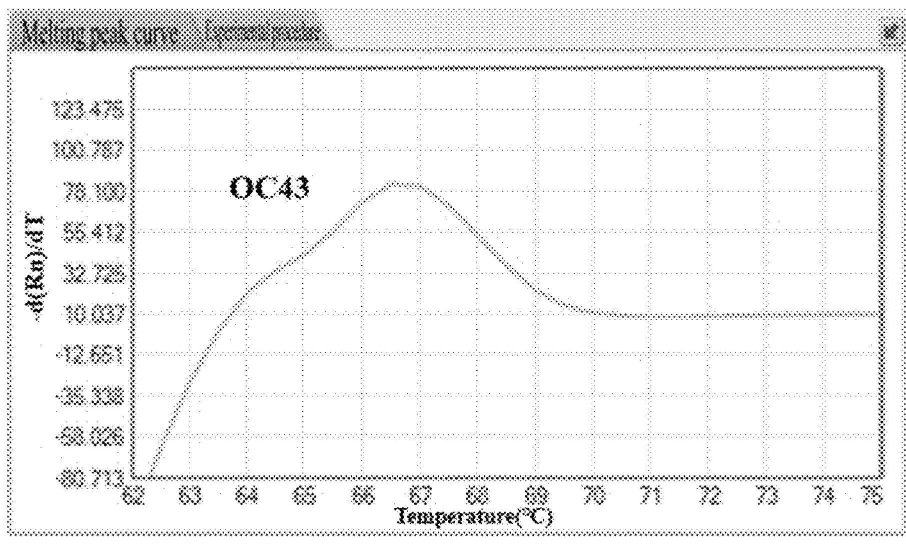
FIG. 5: A is a melting curve diagram of the composition in Table 1 of the present invention for detecting coronavirus OC43; B is a melting curve diagram of the composition in Table 2 of the present invention for detecting coronavirus OC43; C is a melting curve diagram of the composition in Table 3 of the present invention for detecting coronavirus OC43.
Figure 5:
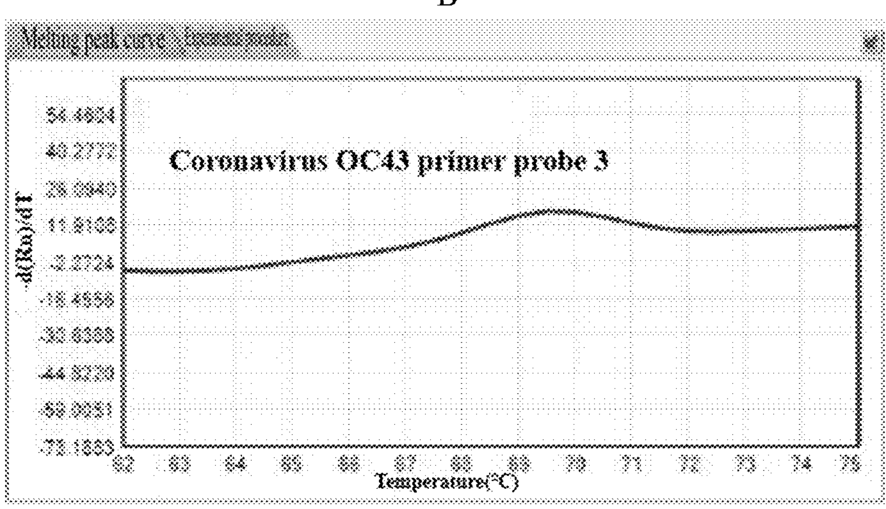
Figure 5:
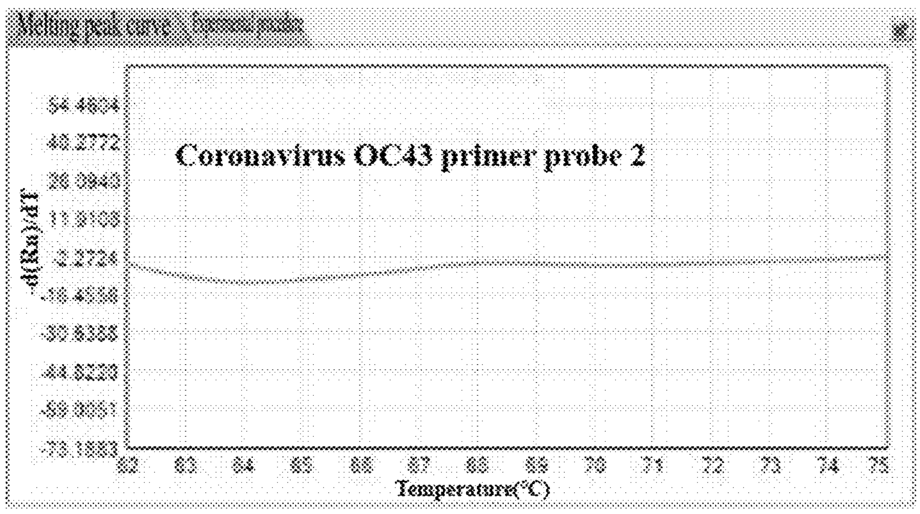
Figure 6:
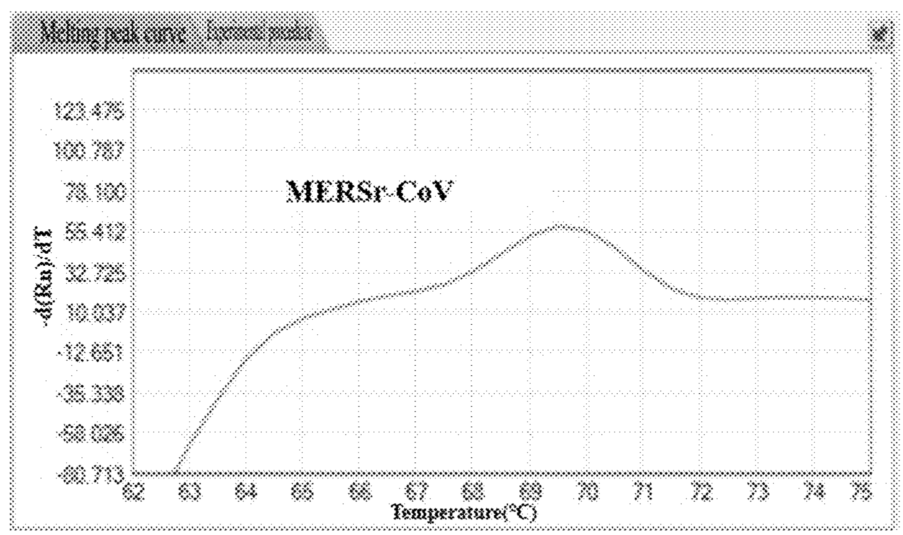
FIG. 6: A is a melting curve diagram of the composition in Table 1 of the present invention for detecting coronavirus MERSr-CoV; B is a melting curve diagram of the composition in Table 2 of the present invention for detecting coronavirus MERSr-CoV; C is a melting curve diagram of the composition in Table 3 of the present invention for detecting coronavirus MERSr-CoV.
Figure 6:
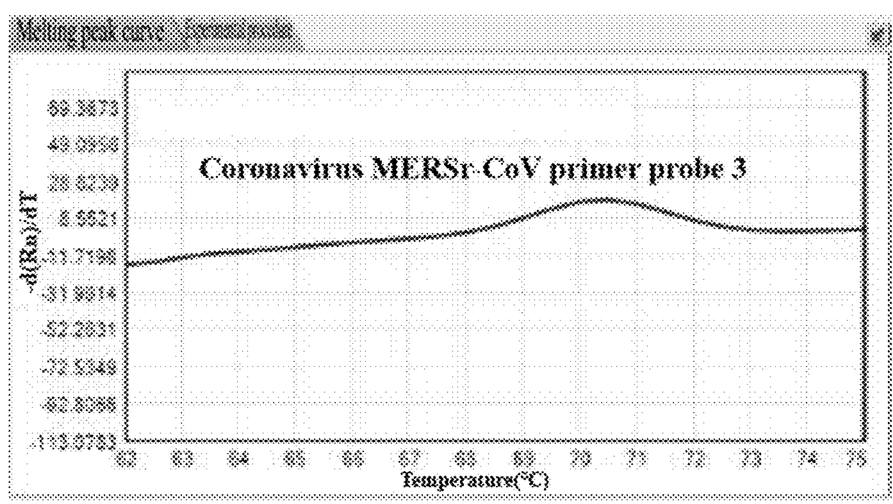
Figure 6:
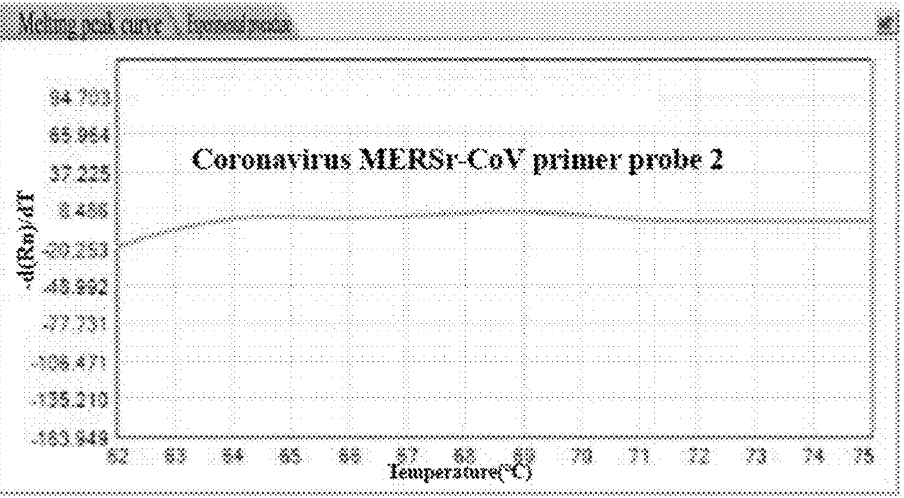
Figure 7:
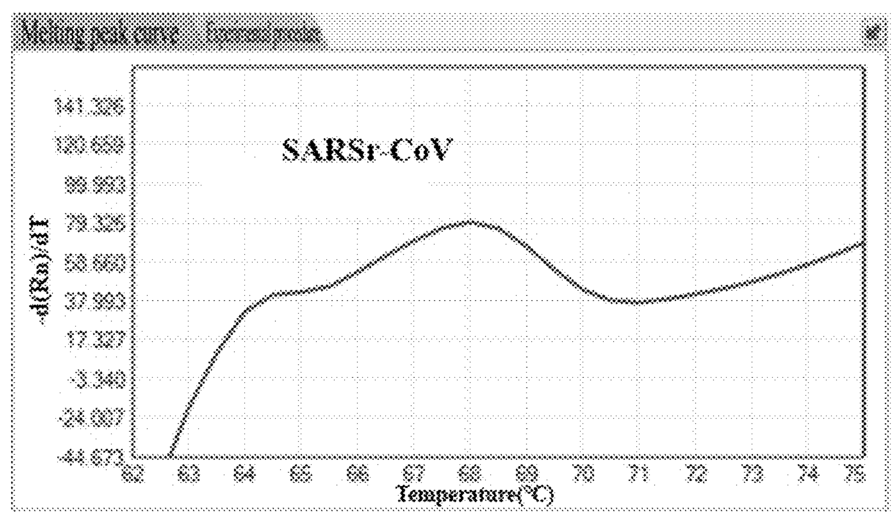
FIG. 7: A is a melting curve diagram of the composition in Table 1 of the present invention for detecting coronavirus SARSr-CoV; B is a melting curve diagram of the composition in Table 2 of the present invention for detecting coronavirus SARSr-CoV; C is a melting curve diagram of the composition in Table 3 of the present invention for detecting coronavirus SARSr-CoV.
Figure 7:
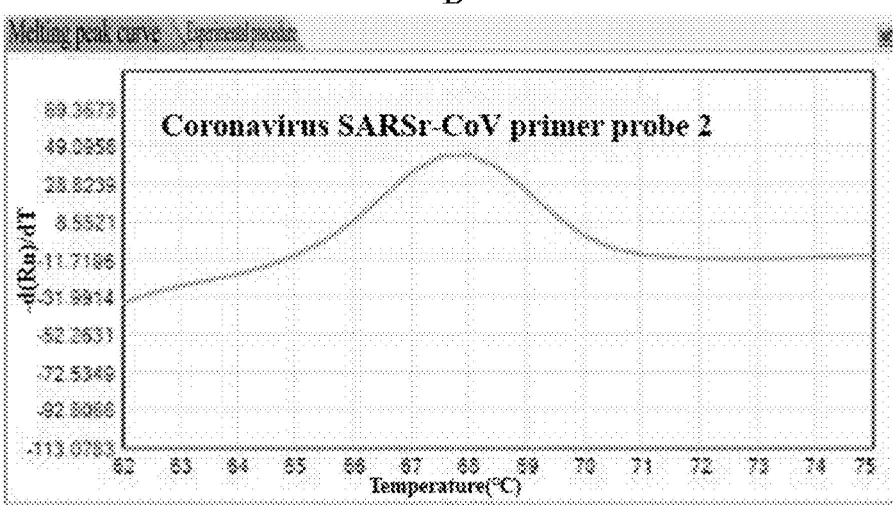
Figure 7:
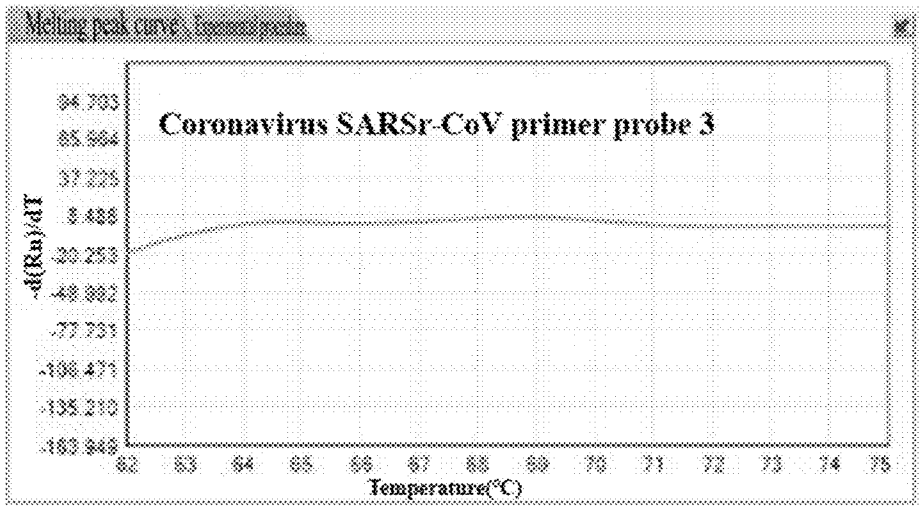
Figure 8:
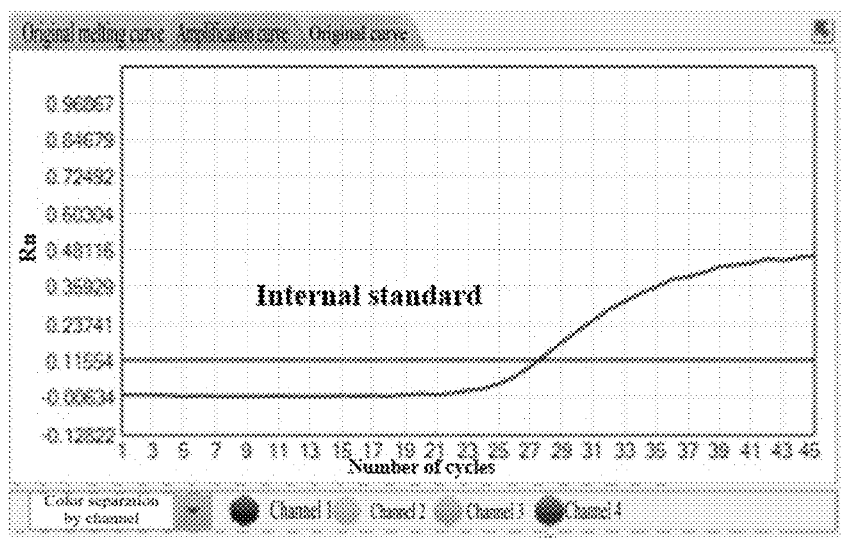
FIG. 8: A is an amplification curve diagram of the composition in Table 1 of the present invention for detecting an internal standard; B is an amplification curve diagram of the composition in Table 2 of the present invention for detecting an internal standard; C is an amplification curve diagram of the composition in Table 3 of the present invention for detecting an internal standard.
Figure 8:
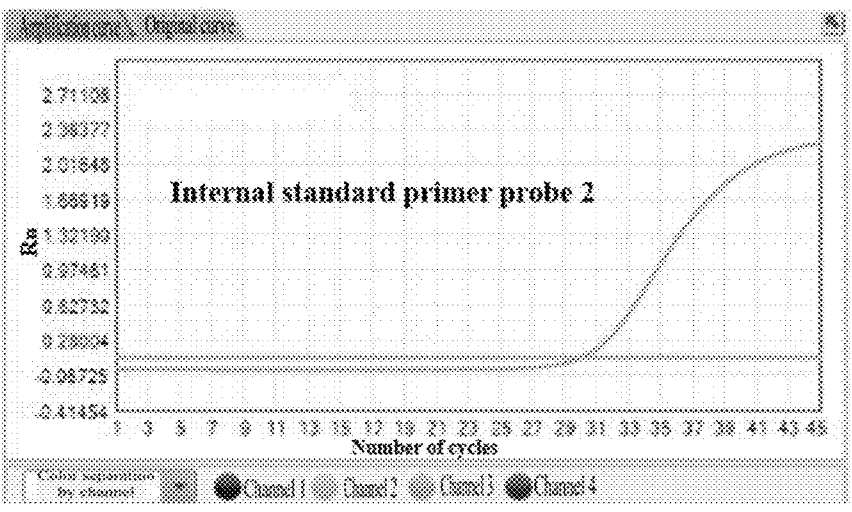
Figure 8:
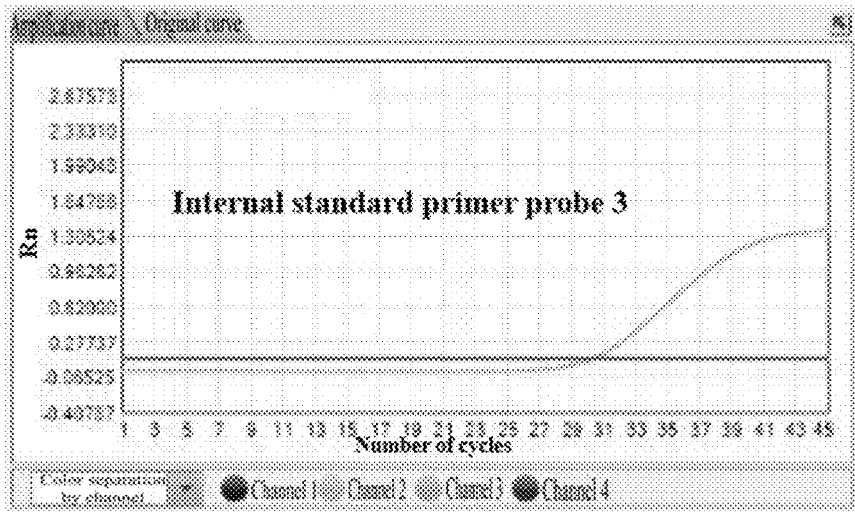

Embodiment 3. Detection Results of Detecting the Positive Control by the Composition of the Present Invention The compositions in Tables 1 to 3 of the present invention were used to test each target-positive plasmid according to the method described in Example 2, so as to simulate a clinical sample. Multiple PCR tests were conducted on a Hongshi fluorescent quantitative PCR instrument. The results are as shown in FIGS. 1-8. As can be seen from the figures:

When the coronavirus 2019-nCoV was detected with the composition in Table 1, the Ct value was around 25; when the coronavirus 2019-nCoV was detected with the composition in Table 2, the Ct value was around 28; and when the coronavirus 2019-nCoV was detected with the composition in Table 3, the Ct value was around 32. The amplification curves of A, B, and C were all relatively steep.

When the coronavirus NL63 was detected with the composition in Table 1, the Ct value was around 30; when the coronavirus NL63 was detected with the composition in Table 2, the Ct value was around 29, but the curve of B was not as steep as that of A; and when the coronavirus NL63 was detected with the composition in Table 3, the Ct value was around 34, and there was basically no amplification curve.

When the coronavirus HKU1 was detected with the composition in Table 1, the Ct value was around 25; when the coronavirus HKU1 was detected with the composition in Table 2, the Ct value was around 30; and when the coronavirus HKU1 was detected with the composition in Table 3, the Ct value was around 34, and the amplification curves of A and B were both relatively steep, and C basically had no amplification curve.

When the coronavirus 229E was detected with the composition in Table 1, the characteristic peak was obvious; when the coronavirus 229E was detected with the composition in Table 2, the characteristic peak was relatively obvious; and when the coronavirus 229E was detected with the composition in Table 3, the characteristic peak was not obvious.

When the coronavirus OC43 was detected with the composition in Table 1, the characteristic peak was obvious; when the coronavirus OC43 was detected with the composition in Table 2, the characteristic peak was relatively obvious; and when the coronavirus OC43 was detected with the composition in Table 3, the characteristic peak was not obvious.

When the coronavirus MERSr-CoV was detected with the composition in Table 1, the characteristic peak was obvious; when the coronavirus MERSr-CoV was detected with the composition in Table 2, the characteristic peak was relatively obvious; and when the coronavirus MERSr-CoV was detected with the composition in Table 3, the characteristic peak was not obvious.

When the coronavirus SARSr-CoV was detected with the composition in Table 1, the characteristic peak was obvious; when the coronavirus SARSr-CoV was detected with the composition in Table 2, the characteristic peak was relatively obvious; and when the coronavirus SARSr-CoV was detected with the composition in Table 3, the characteristic peak was not obvious.

When the internal standard was detected with the composition in Table 1, the Ct value was around 27; when the internal standard was detected with the composition in Table 2, the Ct value was around 30; and when the internal standard was detected with the composition in Table 3, the Ct value was around 31, and the amplification curves of A and B were both relatively steep, while the amplification curve of C was not steep.

What is claimed is:

1. A composition capable of detecting and typing coronaviruses, the composition comprising:

a first group:

a novel coronavirus 2019-nCoV forward primer as shown in SEQ ID NO: 1, a novel coronavirus 2019-nCoV reverse primer as shown in SEQ ID NO: 2, and a novel coronavirus 2019-nCoV probe as shown in SEQ ID NO: 3;

a coronavirus NL63 forward primer as shown in SEQ ID NO: 4, a coronavirus NL63 reverse primer as shown in SEQ ID NO: 5, and a coronavirus NL63 probe as shown in SEQ ID NO: 6; and a coronavirus HKU1 forward primer as shown in SEQ ID NO: 7, a coronavirus HKU1 reverse primer as shown in SEQ ID NO: 8, and a coronavirus HKU1 probe as shown in SEQ ID NO: 9; and a second group:

a coronavirus 229E forward primer as shown in SEQ ID NO: 10 and a coronavirus 229E reverse primer as shown in SEQ ID NO: 11;

a coronavirus OC43 forward primer as shown in SEQ ID NO: 12 and a coronavirus OC43 reverse primer as shown in SEQ ID NO: 13;

a coronavirus MERSr-COV forward primer as shown in SEQ ID NO: 14 and a coronavirus MERSr-COV reverse primer as shown in SEQ ID NO: 15; and a coronavirus SARSr-COV forward primer as shown in SEQ ID NO: 16 and a coronavirus SARS-COV reverse primer as shown in SEQ ID NO: 17, wherein the novel coronavirus 2019-nCoV probe is labeled with a fluorescent reporter group; the coronavirus NL63 probe is labeled with a fluorescent reporter group; and the coronavirus HKU1 probe is labeled with a fluorescent reporter group; and wherein the coronavirus 229E forward primer is labeled with a fluorescent reporter group; the coronavirus OC43 forward primer is labeled with a fluorescent reporter group; the coronavirus MERSr-COV forward primer is labeled with a fluorescent reporter group; and the coronavirus SARSr-COV forward primer is labeled with a fluorescent reporter group;

wherein fluorescent reporter groups in the first group are different from one another, and fluorescent reporter groups in the second group are different from one another.

2. The composition according to claim 1, wherein the composition further comprises an internal standard forward primer as shown in SEQ ID NO: 18, an internal standard reverse primer as shown in SEQ ID NO: 19, and an internal standard probe as shown in SEQ ID NO: 20.

3. The composition according to claim 1, wherein the fluorescent reporter group is selected from the group consisting of FAM, HEX, ROX, VIC, CY5, 5-TAMRA, TET, CY3, and JOE.

4. The composition according to claim 1, wherein the fluorescent reporter group of the novel coronavirus 2019-nCoV probe as shown in SEQ ID NO: 3 is FAM; the fluorescent reporter group of the coronavirus NL63 probe as shown in SEQ ID NO: 6 is HEX; and the fluorescent reporter group of the coronavirus HKU1 probe as shown in SEQ ID NO: 9 is ROX.

5. The composition according to claim 1, wherein the fluorescent reporter group of the coronavirus 229E forward primer as shown in SEQ ID NO: 10 is FAM; the fluorescent reporter group of the coronavirus OC43 forward primer as shown in SEQ ID NO: 12 is HEX; the fluorescent reporter group of the coronavirus MERSr-COV forward primer as shown in SEQ ID NO: 14 is ROX; and the fluorescent reporter group for the coronavirus SARSr-COV forward primer as shown in SEQ ID NO: 16 is CY5.

6. The composition according to claim 1, wherein the coronavirus being detected and typed is selected from the group consisting of novel coronavirus 2019-nCoV, coronavirus 229E, coronavirus NL63, coronavirus OC43, coronavirus HKU1, coronavirus MERSr-COV, and coronavirus SARSr-CoV.

7. The composition according to claim 1, wherein the amount of the primer in the composition is 50-150 nM.

8. The composition according to claim 1, wherein the amount of the probe in the composition is 25-75 nM.

9. A kit for detecting and typing coronaviruses, wherein the kit comprises the composition according to claim 1.

10. The kit according to claim 9, wherein the kit further comprises a nucleic acid release reagent, a dNTP, a reverse transcriptase, a DNA polymerase, and a PCR buffer.

11. The kit according to claim 9, wherein the amount of the primer in the composition is 50 to 150 nM.

12. The kit according to claim 9, wherein the amount of the probe in the composition is 25 to 75 nM.

13. The kit according to claim 10, wherein the concentration of the reverse transcriptase is 5 U/μL to 15 U/μL.

14. The kit according to claim 10, wherein and the concentration of the DNA polymerase is 5 U/μL to 15 U/μL.

15. A method for detecting and typing coronaviruses, wherein the method comprises the steps of:

1) releasing a nucleic acid of a testing sample;
2) performing fluorescent quantitative PCR amplification and detection on the nucleic acid obtained in step 1) by using the composition according to claim 1, wherein the composition comprises primers and probes for coronaviruses; and
3) obtaining detection results comprising amplification curves, Ct values, melting curves and Tm values; and
4) analyzing the detection results to determine the type of coronavirus according to the Ct values and Tm values.

16. The method according to claim 15, wherein the sample is selected from the group consisting of a throat swab, sputum, a bronchoalveolar lavage fluid, and blood.

17. The method according to claim 15, wherein reaction conditions of the fluorescent quantitative PCR are as follows, wherein the melting curve analysis step is performed to obtain Tm values of amplification products, which are used together with Ct values to determine the type of coronavirus:

| Step | Temperature | Time | Number of cycles |
|---|---|---|---|
| Reverse transcription | 50° C. | 25-35 minutes | 1 |
| Pre-denaturation | 94° C. | 2-10 minutes | 1 |
| Denaturation | 94° C. | 10-20 seconds | 45-50 |
| Annealing and simultaneous extension | 60° C. | 20-40 seconds | |
| Melting curve analysis | 50° C. to 95° C. | Fluorescence is collected every 0.5° C. rise. | 1 |

* * * * *